United States Patent
Fischer et al.

(10) Patent No.: US 9,844,414 B2
(45) Date of Patent: Dec. 19, 2017

(54) SYSTEM AND METHOD FOR ROBOTIC SURGICAL INTERVENTION IN A MAGNETIC RESONANCE IMAGER

(76) Inventors: Gregory S. Fischer, Jamaica Plain, MA (US); Gregory A. Cole, Worcester, MA (US); Julie G. Pilitsis, Albany, NY (US)

(*) Notice: Subject to any disclaimer, the term of this patent is extended or adjusted under 35 U.S.C. 154(b) by 319 days.

(21) Appl. No.: 12/873,152

(22) Filed: Aug. 31, 2010

(65) Prior Publication Data

US 2011/0077504 A1 Mar. 31, 2011

Related U.S. Application Data

(60) Provisional application No. 61/238,405, filed on Aug. 31, 2009.

(51) Int. Cl.

| | |
|---|---|
| *A61B 19/00* | (2006.01) |
| *A61B 5/055* | (2006.01) |
| *A61B 34/30* | (2016.01) |
| *A61B 90/00* | (2016.01) |

(52) U.S. Cl.
CPC ........ *A61B 34/30* (2016.02); *A61B 2034/301* (2016.02); *A61B 2090/374* (2016.02)

(58) Field of Classification Search
CPC ..................... A61B 2019/5236; A61B 19/2203
See application file for complete search history.

(56) References Cited

U.S. PATENT DOCUMENTS

2008/0161830 A1* 7/2008 Sutherland et al. .......... 606/130
2008/0306375 A1* 12/2008 Sayler et al. ................. 600/417

FOREIGN PATENT DOCUMENTS

WO WO2007/141784 12/2007

OTHER PUBLICATIONS

Fischer, "MRI-Compatible Pneumatic Robot for Transperineal Prostate Needle Placement", IEEE/ASME Transactions on Mechatronics, vol. 13, No. 3, Jun. 2008, pp. 295-305.*
Krieger et al, Design of a novel MRI compatible manipulator for image guided prostate interventions, IEEE Transactions on Biomedic., vol. 52 Issue: 2.*
Wang, Y. et al., "MRI Compatibility Evaluation of a Piezoelectric Actuator System for a Neural Interventional Robot," 31st Annual International Conference of the IEEE EMBS, Minneapolis, Minnesota, Sep. 2-6, 2009.
Cole, G. et al. "Design of a Robotic System for MRI-Guided Deep Brain Stimulation Electrode Placement," 2009 IEEE International Conference on Robotics and Automation, Kobe, Japan, May 12-17, 2009.

* cited by examiner

*Primary Examiner* — Serkan Akar
(74) *Attorney, Agent, or Firm* — Michael G. Johnston; Moore & Van Allen, PLLC

(57) ABSTRACT

A system and method for image guided assisted medical procedures using modular units, such that a controller, under the direction of a computer and imaging device, can be utilized to drive and track low cost, purpose specific manipulators. The system utilizes modular actuators, self tracking, and linkages. The system can be optimized at a low cost for most effectively performing surgical procedures, while reusing the more costly components of the system, e.g. the control, driving, and tracking systems. The system and method may utilize MRI real time guidance during the above procedures.

20 Claims, 16 Drawing Sheets

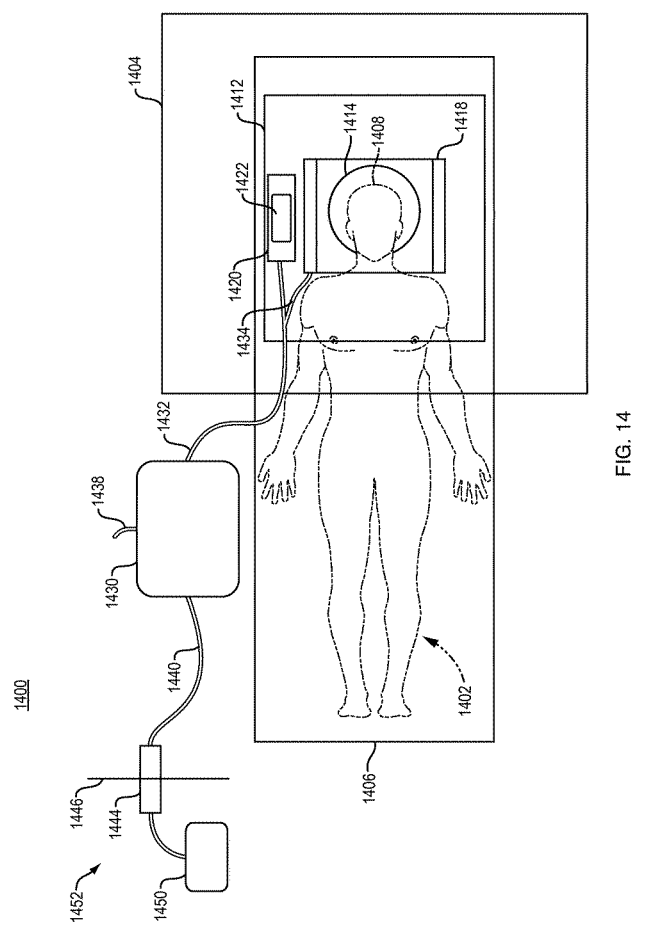

SYSTEM AND METHOD FOR ROBOTIC SURGICAL INTERVENTION IN A MAGNETIC RESONANCE IMAGER

CROSS REFERENCE TO RELATED APPLICATIONS

This application claims priority to a U.S. provisional application Ser. No. 61/238,405 entitled SYSTEM AND METHOD FOR ROBOTIC SURGICAL INTERVENTION, filed on Aug. 31, 2009 which is incorporated in its entirety herein by reference.

FIELD OF INVENTION

The present teachings relate generally to the field of guidance equipment and, more particularly, to equipment that is used to aid in the accurate guidance of surgical tools and/or sensors to locations in the human body.

BACKGROUND

While the field of image guided surgical robotic assistance is still in its infancy, it is expanding rapidly. The benefit of image guided robotically assisted surgery is fairly clear: the combination of computer controlled precision movement and high resolution soft tissue imaging allows the surgeon to accomplish the procedural goals with minimized damage to surrounding tissue. There are many organizations across the globe developing imaging compatible systems of, though currently few are on the market. Most research facilities are either attempting to re-build general purpose serial manipulators for imaging compatibility, or developing single purpose units to perform a multitude of tasks on a single area of the body.

Stereotactic neural intervention is a commonly practiced surgical procedure today. There are many treatments and operations that require the accurate targeting of, and intervention with, a specific area of the brain which utilize stereotactic neural intervention. One common use of this procedure is Deep Brain Stimulation (DBS), which is often used for the treatment of Parkinson's Disease.

Magnetic resonance imaging (MRI) compatible systems have been developed, though they typically manually driven, bulky and/or inconvenient to use. There are systems for specific procedures such as DBS therapy, though those systems are inconvenient to use and/or lack accuracy due to the lack of real time image guidance.

DBS is a technique for influencing brain function through the use of implanted electrodes. Direct magnetic resonance (MR) image guidance during DBS insertion would provide many benefits; most significantly, interventional MRI can be used for planning, real-time monitoring of tissue deformation, insertion, and placement confirmation. The accuracy of standard stereotactic insertion is limited by registration errors and brain movement during surgery. With real-time acquisition of high-resolution MR images during insertion, probe placement can be confirmed intraoperatively. Direct MR guidance has not taken hold because it is often confounded by a number of issues including: MR compatibility of existing stereotactic surgery equipment and patient access in the scanner bore. The high resolution images required for neurosurgical planning and guidance require high-field MR (1.5-3T); thus, any system must be capable of working within the constraints of a closed, long-bore diagnostic magnet. Currently, no technological solution exists to assist MRI guided neurosurgical interventions in an accurate, simple, and economical manner.

Currently, a typical DBS placement procedure is comprised of the following events:
1. Patient arrives at hospital for pre-procedure MRI scan.
2. Surgeons analyze the patient's images, and produces a surgical plan.
3. Patient returns to the hospital where a stereotactic surgical frame is attached to the skull in the operating room.
4. A computed tomography (CT) scan is taken of the patient with the frame to register the surgical plan to the frame.
5. The surgical frame is manually aligned and used to guide a drill for drilling the burr holes to gain access to the cranial cavity.
6. The surgical frame is used to guide the placement of electrodes through the burr hole.
7. Some form of placement confirmation is utilized (often micro electrode recordings, fluoroscopy, or computed tomography.)
8. Often the procedure is repeated for bilateral insertion of a second electrode.
8. Patient is sent to recovery.

This process has been used for several decades, though tissue deformation can cause registration errors between the preoperative images used to create the surgical plan, and the state of the patients anatomy during the procedure. These errors can lead to a host of negative side effects including: reduced effectiveness of the DBS equipment, unwanted neurological changes (mood shift, chronic gambling), brain injury, brain hemorrhage, etc.

This procedure has several other drawbacks, such as the following:
during the time between when the surgical plan is generated and the procedure occurs, there is a possibility of soft tissue shift within the patient, causing inaccurate placement of electrodes;
when the cerebrospinal fluid drains after the first burr hole is drilled, there is another possibility of soft tissues shift;
for some applications of DBS, micro electrode recordings cannot be used for placement confirmation due to a high possibility of causing brain damage;
shifts in soft tissue increase the risk of a blood vessel being moved into the surgical path, which could cause brain hemorrhage; and
electrode insertion itself will cause tissue deformation as it is being inserted into the operative area.

Therefore, it would be beneficial to have a superior system and method for performing a plurality of robotic surgical interventions utilizing real-time MRI imaging.

SUMMARY

The needs set forth herein as well as further and other needs and advantages are addressed by the present embodiments, which illustrate solutions and advantages described below.

The system of the present invention is based on embodiments which use modular units, such that a controller can be utilized to drive and track low cost, purpose specific manipulators. The system utilizes modular actuators, self tracking, and linkages constructed from, for example, but not limited to, hard image compatible plastics that are not ferro magnetic, although under other circumstances such as, where magnetics are not utilized, ferro magnetic material may be used. Therefore, the system can be optimized at a low cost for most effectively performing a plurality of individual surgical procedures, while reusing the more costly components of the system, e.g. the control, driving, and tracking systems.

In one embodiment the system comprises a manipulator linkage which targets DBS electrode placement and allows the procedure to be performed based on interactively updated MRI images. Alternatively, the system may be used to perform the procedure based almost entirely on pre operative images in a manner similar to the typical approach in the operating room. The system is a safe and reliable electrode placement assistant that overcomes the difficulties of working in a closed high-field MRI. The objective of the system, but is not limited to, enables registering and placing electrodes within the brain under image guidance with half millimeter accuracy. The system reduces procedure time, cost, and complications while improving effectiveness and availability.

The method of the present embodiment includes, but is not limited to, MRI-compatible self-positioning stereotactic surgical guidance that bridges the gap between high resolution imaging modalities and interventional procedures that utilize them for planning purposes.

Further embodiments are used to facilitate MRI guided insertion of electrodes for deep brain stimulation under live imaging. The embodiments comprise a central controller or controller, and actuated manipulator or armature, and a user workstation. The controller of the system contains a computing unit that can process sensor information from the actuated armature as well as generate driving signals to operate the armatures' actuators. Additionally, the central control unit communicates with a user workstation which combines position information from the armature with scanner images in order to register the armatures position within the imaging space, and allow the user to generate position commands for the robotic manipulator.

The method for the design of all of these components has generated a system which produces minimal degradation (that is, almost no visually identifiably interference) on MRI image quality. The modular system is designed to be able to use a wide variety of procedure specific mechanism, with the same controller so that the mechanism can have numerous, limited degrees of freedom and more of the system is precision mechanically constrained. The workstation may register the position of the robotic manipulator relative to the scanner and the patient, at which point the operator may develop or import a surgical plan to interact with the desired intervention points. Once the plan is developed, the operator may perform the procedure under live or real-time imaging guidance.

Thus, the embodiments provide for a modular system for image guided robotic assisted medical procedures. The embodiments of the system comprises a manipulator for a specific medical procedure, a controller, an imaging device and a computer. The controller of the system is connected to the manipulator. The controller directs at least one motion of the manipulator. The controller is also capable of directing at least one other manipulator. The imaging device of the system enables visualization of a tissue at the specific medical procedure. The computer of the system is connected to the imaging device and the controller. The computer collects and processes images from the imaging device and instructs the controller to direct the manipulator. The system of the present invention can also be used when the medical procedure is a surgical procedure. The surgical procedure can be, but is not limited to, a deep brain stimulation procedure.

The embodiments also provide for a method for image guided robotic assisted medical procedures. The method comprises identifying an area of a body for a medical procedure. The method also comprises defining at least one motion of an instrument, this, at least one motion, is required for performing the medical procedure. The method further comprises assembling a manipulator which can be used for the medical procedure. Assembling of the manipulator comprises identifying linkages for performing the above at least one motion, and selecting actuators and sensors for connecting to the linkages. The actuators and sensors are used for controlling movements of the linkages. The method even further comprises connecting the manipulator to a controller which is capable of directing the manipulator. The controller is also capable of directing at least one other manipulator.

Other embodiments of the system and method are described in detail below and are also part of the present teachings and can include work with various other body parts such as, but not limited to, prostates, lungs, breasts, hearts, limbs such as knees, hips and the like.

For a better understanding of the present embodiments, together with other and further aspects thereof, reference is made to the accompanying drawings and detailed description.

BRIEF DESCRIPTION OF THE DRAWINGS

FIG. 14 illustrates the basic system configuration of an embodiment of the present invention.

DETAILED DESCRIPTION

The present teachings are described more fully hereinafter with reference to the accompanying drawings, in which the present embodiments are shown. The following description is presented for illustrative purposes only and the present teachings should not be limited to these embodiments. In addition, the publication entitled, "MRI Compatibility Evaluation of a Piezoelectric Actuator System for a Neural Interventional Robot," authored by Yi Wang' Gregory A. Cole, Hao Su, Julie G. Pilitsis and Gregory Fischer, presented at the 31$^{st}$ Annual International Conference of the IEEE EMBS, Minneapolis, Minn., USA, Sep. 2-6, 2009 is incorporated in its entirety by reference.

Figure 1A:
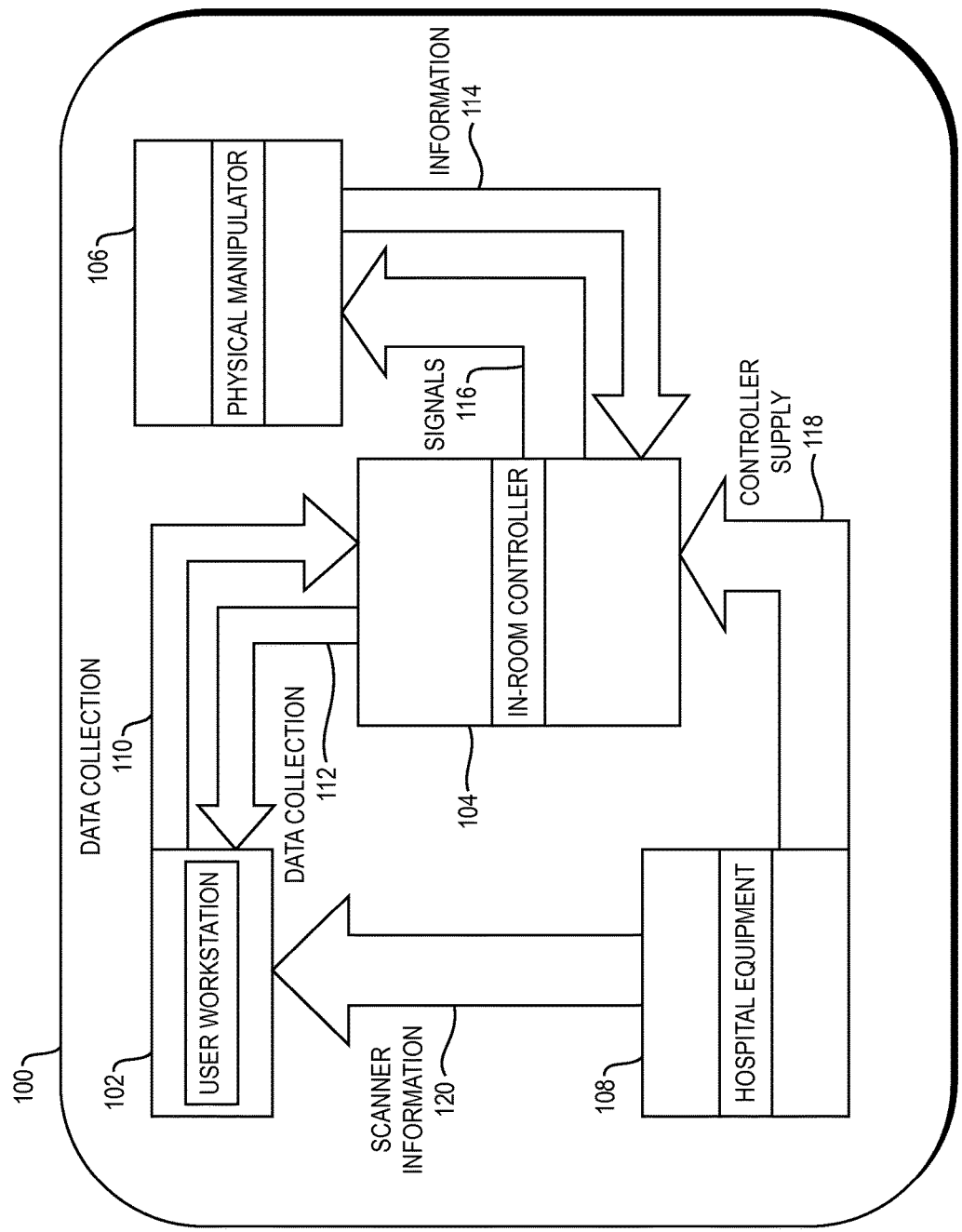
FIGS. 1A and 1B block diagrams illustrating a design of the system architecture.
Figure 1B:
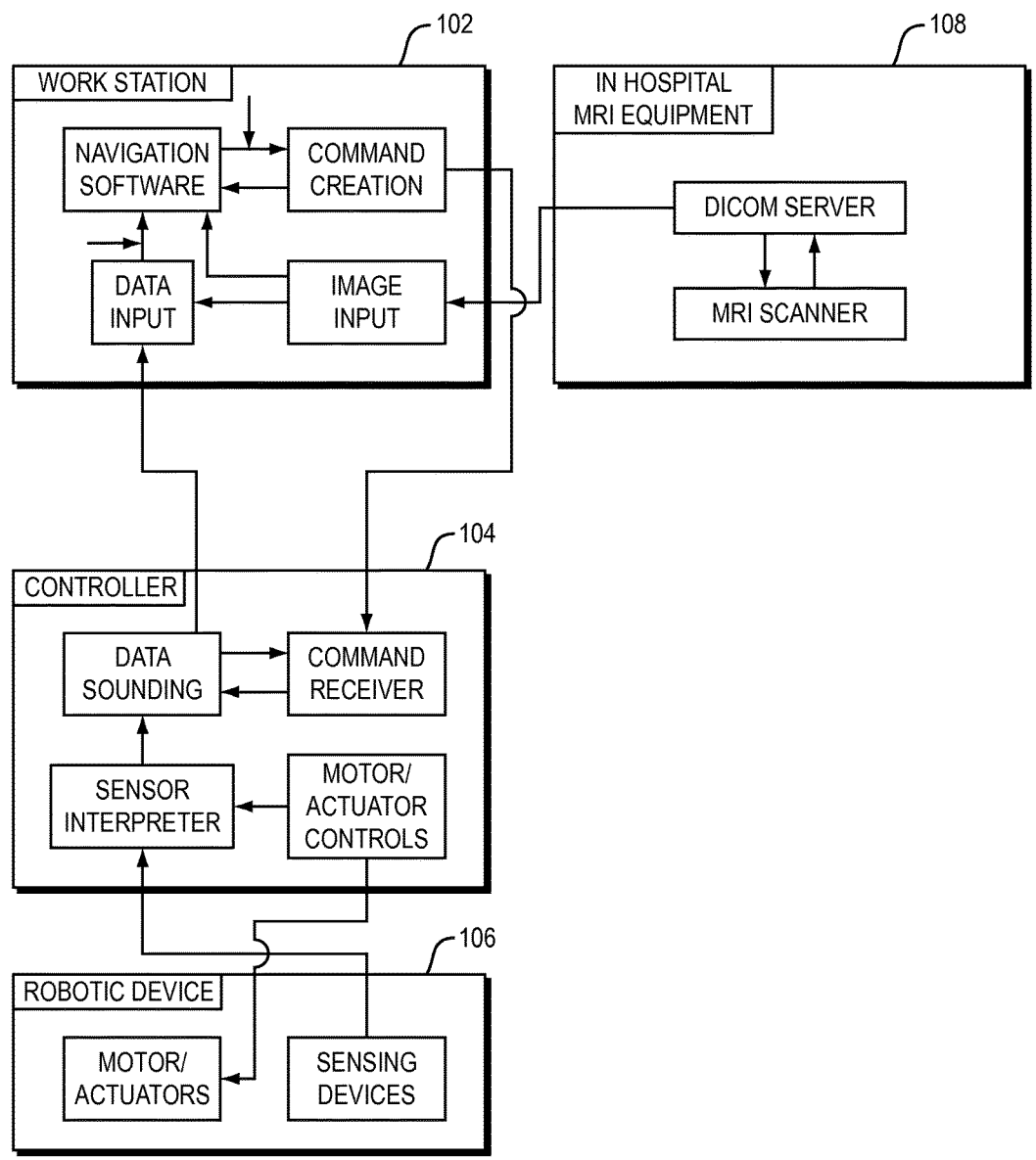

Referring now to FIG. 1, shown is a block diagram depicting an embodiment of the system architecture. The system 100 comprises a workstation 102, a controller 104, a robotic device or manipulator 106. Also shown is the clinical equipment or hospital equipment 108 that may cooperate with the system. The user workstation 102 serves as a planning and navigation workstation for the user. Workstation 102 may be, but is not limited to, a laptop computer located in an MRI scanner's console room. Alternatively, it may be a separate computer, integrated into the medical imaging equipment, or a part of a standalone system (not shown). Workstation 102 is communicative coupled via data connections or couplings 110 and 112 to the robot controller 104 which, in one embodiment, is located inside the MRI scanner room and coupled via fiber optic communications. Alternatively, coupling 110 and 112 may be a shielded cable or wireless link. The workstation 102 sends commands and registration to the robotic device or manipulator 106 via 110 and receives robot status and location via connection 112. In one embodiment, the controller 104 receives alternating current (AC) power from the scanner room via a grounded cable 118. Alternatively, direct current (DC) power may be directly supplied or a battery may be used to provide power. The physical manipulator 106 can be the robotic device that interacts with the patient. It typically is MRI compatible and sits inside an MRI scanner bore while performing an intervention. Manipulator 106 is coupled to controller 104 via information connectors or signals 114 and 116. Connector 114 provides the robot controller 104 with information from the robot's sensors, including the position of the controller or manipulator 104. Connector 114 may be an electrical connection containing one or more channels from, for example, an optical encoder utilizing a differential signal output. Alternatively, it may provide a digital or analog digital from other encoder or potentiometer. Position sensing may alternatively be performed using fiber optics that communicate along connection 114. Connection 114 may also include pressure, force, torque, or other sensory information. Connection 116 provides control signals to the manipulator's actuators. In one embodiment, connection 116 is a shielded electrical cable that provides a drive signal to piezoelectric motors. Alternatively, connection 116 may transmit pneumatic or hydraulic power to the manipulator 106. Manipulator 106 performs the surgical intervention. In one embodiment, manipulator 106 is an actuated frame for assisting deep brain stimulation lead placement inside an MRI scanner. In one embodiment, the manipulator 106 is composed of two separable components, a motor module and an application-specific or patient-specific mechanism.

Hospital equipment 108 can include the medical imaging equipment. In one embodiment, equipment 108 includes an MRI scanner. The MRI scanner transmits images via communication coupling 120 to the workstation 102. The workstation 102 can operate software which tracks a patient anatomy and generates the user interface overlaying the position of the manipulator 106. This workstation 102 is designed to contain all of the software utilized to interface with the user and manages a large portion of the high power processing such as three dimensional image creation and analysis. The software facilitates interactions with the MRI scanner located in the equipment 108 and the controller 104 of the system 100. The workstation 102 may communicate with an image server located in hospital equipment 108 associated with the MRI so that images generated by the scanner may be utilized by the navigation software. The images may be transferred via a Digital Imaging and Communications in Medicine (DICOM) server, direct connection, real-time streaming, or other means. In one embodiment, the workstation 102 can also send commands to the MRI scanner to control scan parameters including, but not limited to, scan plane location, scan plane orientation, field of view, image update rate and resolution. The workstation 102 may first register the position of the robotic device or manipulator 106 relative to the patient or imaging system, at which point the operator may develop a surgical plan to interact with the desired intervention points. Once the plan is developed, the operator may perform the procedure under live imaging or real-time guidance so that during the procedure the operator will be able to confirm that the intervention axis is oriented optimally for insertion. Additionally, the operator will be able to confirm the placement of surgical instruments at desired locations.

In one embodiment, the manipulator 106 is mechanically coupled to a platform placed upon the bed of the MRI scanner, wherein the platform also includes imaging coils and head fixation. In a further embodiment, the controller 104 also controls the orientation of the MRI imaging coil to align an opening with the planned robot trajectory. The imaging coil may be controlled by the robot controller or controller 104 or by other means such that it may be reconfigured to optimize patient access while maintaining image quality. Further, the manipulator 106 and the platform may also incorporate active or passive tracking fiducials or coils to localize the robot in the MRI scanner. In alternate embodiment, the manipulator 106 is coupled to a head frame and/or operating room table and the controller 104 is also located in the operating room.

This system 100 of the present invention is, essentially, a high precision, closed loop system that can be used to compile MRI image slices into three dimensional images, overlay a three dimensional image of a manipulator that can be operated within the scanner bore, select a course of motion for an intervention, and execute the intervention under live image guidance. While this has benefits in the medical world, there are also benefits to other industries where the precision internal images of the MRI can be utilized. Some of the industries used with the system can be instrumental and are, for example, art restoration, plant splicing, and veterinary work. Additionally, while this system is MRI compatible, it is also compatible with most other imaging modalities currently utilized. As such, under other imaging modalities that do not require magnetic compatibility, this system could be utilized, for example, by law enforcement, or manipulation of internal structures of devices.

The system 100 described herein has modular architecture. The system 100 can be integrated into an MRI surgical suite. Individual surgeons or hospitals can use a variety of manipulators 106 or end effectors for the manipulator 106 for the specific procedures that they perform. Alternatively, custom patient-specific modules for the manipulators 106 may be used with the system. A single controller 104 is capable of operating the variety of manipulators 106. This distributes the cost of both equipment and maintenance of the devices in a manner where "everyone just pays for what they use." By distributing the payment structure, different institutions and individuals may be responsible for their own segments of equipment.

In another embodiment, although not limited thereto, the system comprises an MRI-compatible self-positioning surgical guide utilizing a similar procedure planning to stereotactic intervention. This system bridges the gap between high resolution imaging modalities and interventional procedures that utilize them for planning purposes. The system may utilize live MRI guidance during these procedures. Alternate embodiments of the system may be used for applications other than deep brain stimulation such as with other body parts such as prostrates, lungs, hearts, knees and the like. Other neurosurgical procedures may be performed with the present invention including lead placement, thermal and cryogenic ablation, injections, evacuation, and surgical interventions. The invention is not restricted to only the specifically mentioned clinical applications. Further embodiments may be used to access other organ systems including for MRI image-guided prostate brachytherapy, biopsy and ablation.

The system 100 allows the use of in situ MRI guidance during a neural intervention procedure with the added benefit of computer controlled motion for the positioning of a tool guide. In one embodiment, although not limited thereto, the system 100 operates within the scanner bore of a closed-bore, high-field, diagnostic MRI scanner. This device may actively drive the position of the tool guide while leaving an acceptable volume of workspace for performance of the operation by the surgeon. In order to accomplish this, the system 100 may utilize similar planning methods to a manual stereotactic surgical procedure. For instance, although not limited thereto, system 100 may utilize a mechanically constrained remote center of motion (RCM) style linkage, where the RCM point is placed within the cranial volume at the target location. In such a way, the primary insertion axis of the device targets the RCM point no matter where the insertion guide is moved. This allows the operator to set a desired intervention point and insert tools from an arbitrary burr hole location on the skull to reach the same target point. Alternatively, the RCM point may be placed in the more traditional manner at the skull entry point and allow access to a range of target locations through the same burr hole.

Figure 11:
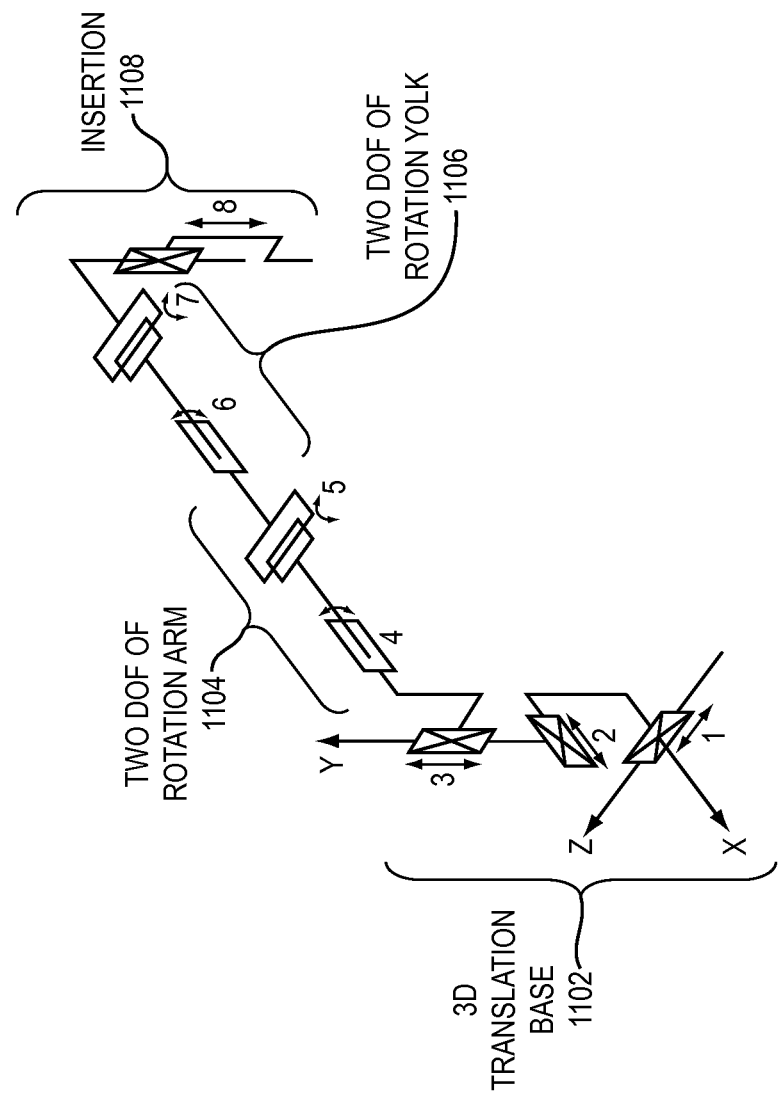
FIG. 11 is a schematic illustration depicting the kinetic equivalency of the eight-degree of freedom embodiment of the manipulator of the system.

The system 100 may also incorporate power transmission, although not limited thereto, that permits the use of modular end effecters to expand the functionality of the system 100 with two additional degrees of freedom (DOF) See FIG. 11. In one embodiment, the system uses an armature that mounts to either side of the patient's skull and is contained within a small volume in order to leave as much room as possible within the scanner bore for the surgeon to move. The system may also be integrated with the tray that the patient rests on during the procedure, although not limited thereto. The system may also be integrated with the MR imaging coil, although not limited thereto.

Figure 2:
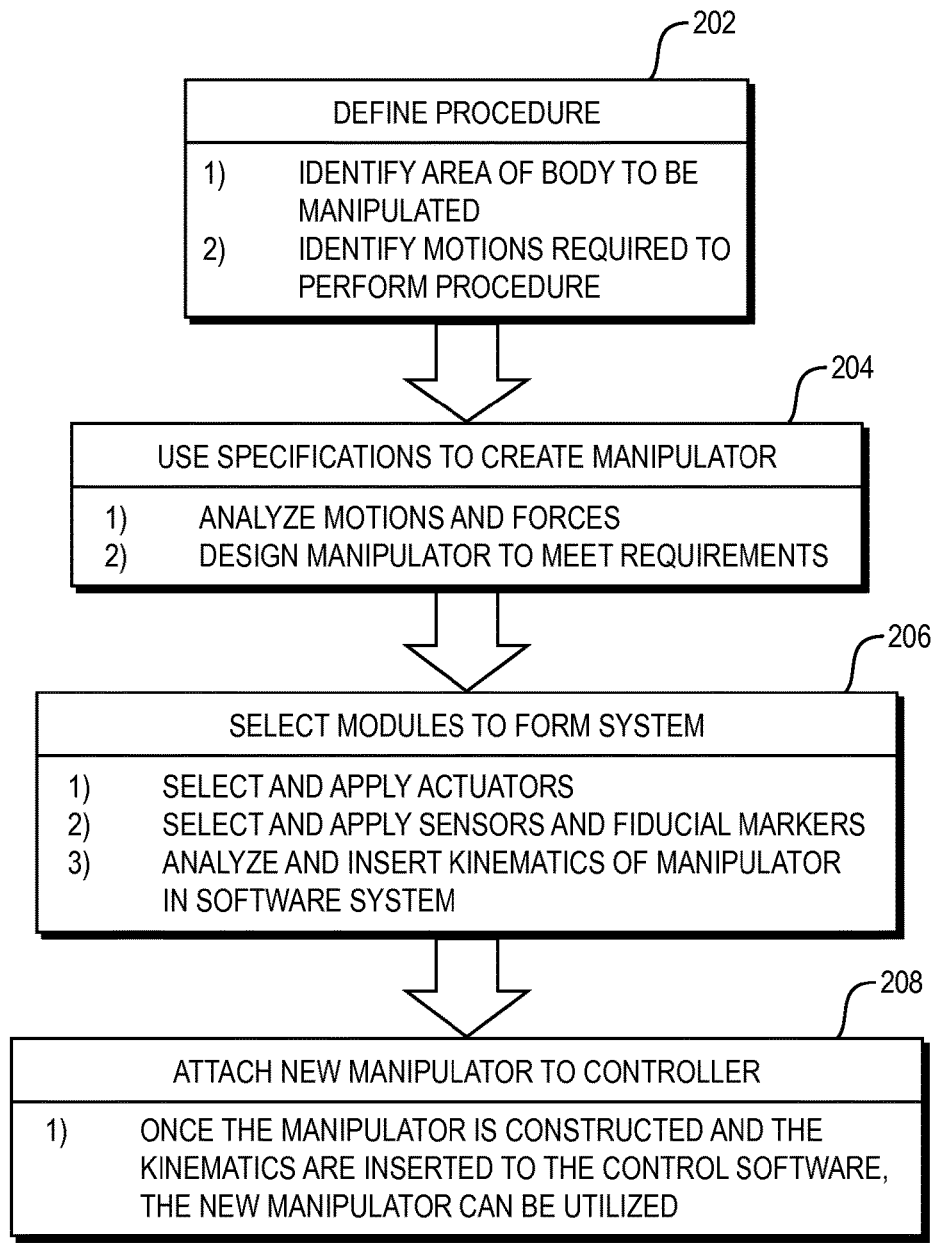
FIG. 2 is a flowchart illustrating a method of the system.

The method of configuring the system 100 of the present invention is illustrated in FIG. 2. The configuration is defined by the medical procedure described in block 202 to be performed by the system 100. The specific procedure and/or patient configuration are used to determine the requirements as described in 204. The requirements are used to select or develop manipulator 106 or end effector as described in 206. The manipulator 106 or end effector 106 is coupled to the robotic system and controller 104.

A method used in system 100 can be as follows:
1) identify the area of the body to be manipulated
2) identify motions required to perform procedure
3) analyze motions and forces
4) design manipulator to meet requirements
5) select and apply actuators
6) select and apply sensors and fiducial markers
7) analyze and insert kinematics of manipulator in software system
8) once the manipulator is constructed and the kinematics are inserted to the control software, the new manipulator can be utilized.

Figure 3:
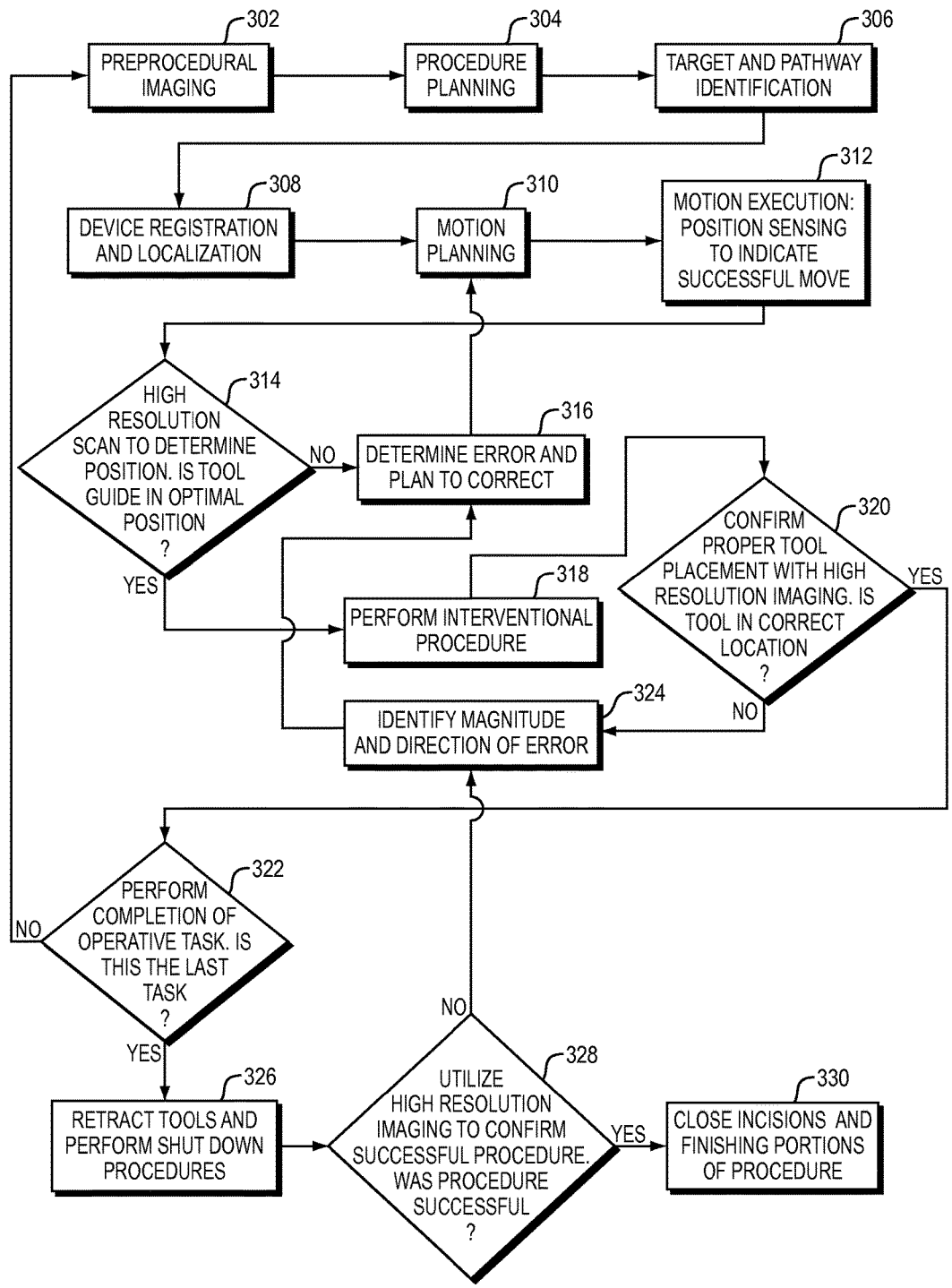
FIG. 3 is a flowchart illustrating a method of using the system.

The method of utilizing the system 100 of the present invention is illustrated FIG. 3. in a flow diagram re-procedural imaging 302 is acquired prior to the intervention. Imaging 302 may include, but is not limited to, anatomical MRI, functional MRI, spectroscopic imaging and computed tomography or the like. These images may be acquired days or weeks before the procedure, or may be performed the day or immediately prior to the intervention. Pre-procedural images 302 are used in medical procedure planning 304. The target or targets are identified 306. This step may be manual, semi-automated, or fully automated. In one embodiment, statistical atlases may be used to assist in locating the target location. A planned trajectory is also identified in 306. This trajectory may be manually generated or it may be generated in an automated or semi-automated fashion. In one embodiment, blood vessels and other critical structures are automatically located and a safe trajectory is planned. Once the procedure is defined, a patient is placed within the bore of a diagnostic scanner. In an embodiment, the patient is placed inside air MRI scanner along with the robotic device or manipulator 106. A series of images are taken of the patient anatomy that the procedure needs to be performed on and used to register the patient with eth pre-procedural plan. This step may also be repeated iteratively or continuously during the procedure. The images are assembled in the workstation 102 of FIG. 1 into a three-dimensional display where the physician can view and modify the medical plan.

The robotic manipulator 106 is localized within the scanner and registered to the patient in 308. Localization may be performed by imaging fiducials, active tracking coils, an external tracking system or other means. The motion plan for the robot is generated based on the relative pose of the robot to the patient and the planned trajectory or target 306. The manipulator 106 is commanded to move and align the surgical tool as described in 312. The surgical tool may be a needle, electrode, marker, drill, drill guide, cannula, ablation probe, laser, or other similar device. Real time or interactive medical images of the manipulator 106 and the patient may be performed during motion 312 to guide alignment. Position sensing on board the manipulator 106 or external to it may be used to guide for alignment. Upon completion of motion or at a stopping point in an iterative insertion, confirmation images are acquired 314. If the tool is not yet at the target location, the plan is updated in 310 and the process is repeated or iterated. In one embodiment, continuous MRI images are used for closed loop control of an electrode, cannula or other instrument. Once placed, the interventional procedure, or a current step within, is performed in 318. Placement is confirmed in 320 and the process may be iterated to ensure appropriate position as defined in 324. In one embodiment, confirmation 320 is performed via micro electrode recordings. In an alternate embodiment, high resolution MRI imaging is utilized. In another embodiment, fluoroscopy or computed tomography imaging confirms appropriate placement. In procedures with multiple stages, the process may be repeated as shown in 322. This may be the result of multiple stages. In one embodiment, the manipulator guide alignment of a surgical drill to generate a burr hole in the skull and then later aligns a guide cannula and an electrode. The robot manipulator 106 may move in and out of position between stages to allow improved patient access. Further, the procedure may be repeated for multiple targets. When complete, the manipulator 106 retracts or is removed 326. Additional validation may be performed to ensure a successful procedure 328 and the procedure is completed 330. For procedural planning, guidance and validation, the MRI imaging may include one or more of: traditional diagnostic imaging, rapid imaging, 3D imaging of arbitrary pose, volumetric imaging, functional imaging, spectroscopic imaging, blood flow sensing, diffusion imaging or other approach. Further, multi-modality imaging may be incorporated to couple MRI imaging with ultrasound or other medical imaging means.

Figure 4:
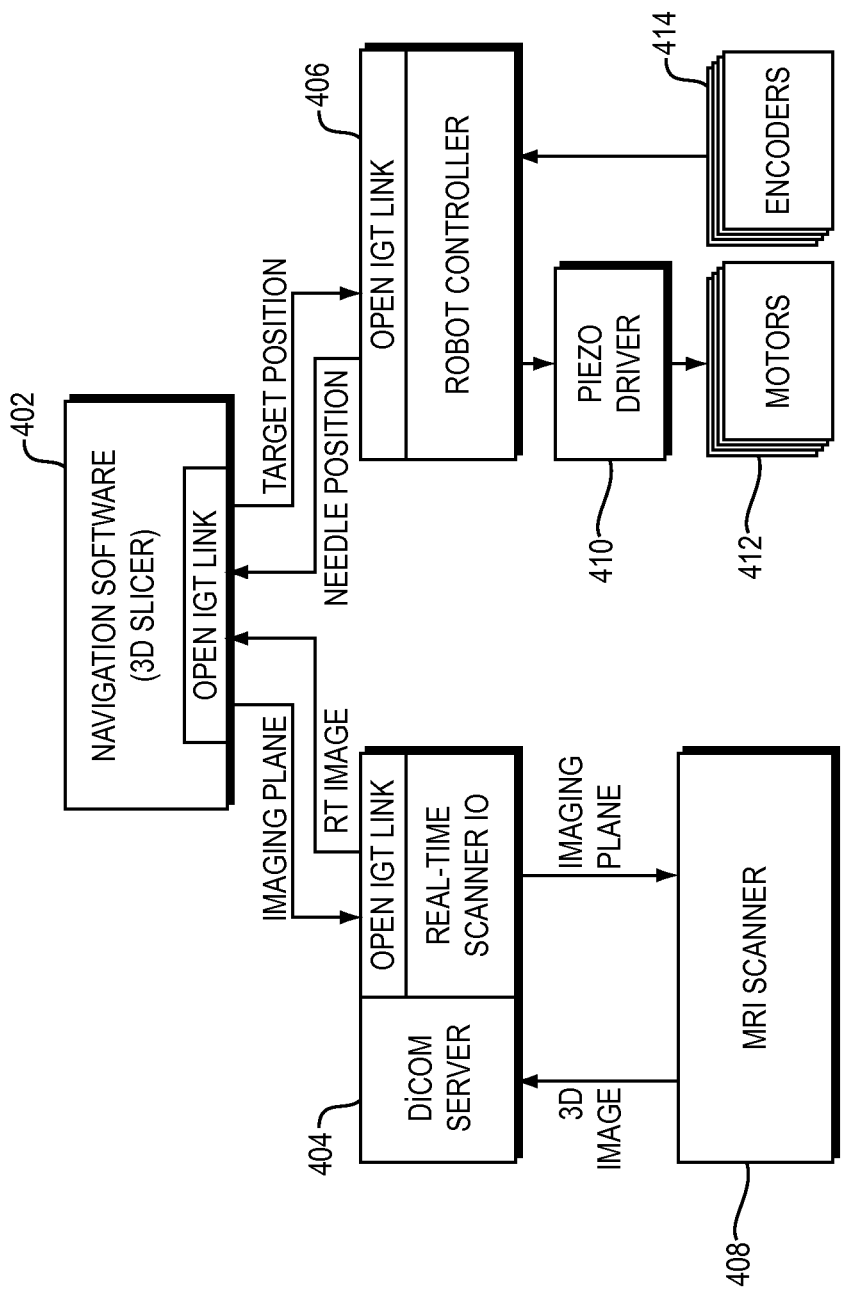
FIG. 4 is a schematic diagram illustrating functional units comprising the controller of the system and their interconnects.

The configuration of one embodiment of system 100 of the present invention is illustrated in the block diagram of FIG. 4. Navigation software 402 is located on workstation 102. The navigation software 402 is used to guide the intervention and may also be used for preoperative and intraoperative planning as described previously. In one embodiment, the navigation software 402 is based on the modular, open source 3D Slicer software. Alternatively, navigation software 402 may be a commercially developed platform. Navigation software 402 is communicative coupled to an MRI medical imaging system or interface computer or interface 404. The communication interface may be an established protocol such as DICOM or OpenIGTLink. Alternate protocols or connections may be utilized. The navigation software 402 may send control signals to the imaging system interface 404 to control scan plane location, orientation or other parameters. In one embodiment, the imaging continuously streams images to the navigation software 402 that visualizes them on workstation 102 of FIG. 1. Imaging system interface 404 controls the MRI scanner or other imaging system 408 and retrieves planar and volumetric image data from the scanner. The robot controller 406 represents the controller 104 of FIG. 1. The controller 104 is communicatively coupled to the navigation software 402. In one embodiment, the coupling is a fiber optic network connection. In an embodiment the navigation software 402 sends commands including, but not limited to, positions, orientations, velocities, and/or forces to the controller 104. In an embodiment, the robot controller 104 incorporates a control computer that receive the data from the navigation software 402 and performs the necessary computations. The computations may include one or more of forward kinematics, inverse kinematics, trajectory generation and registration. The robot controller 104 sends data to navigation software 402 including, but not limited to, the manipulator 106 position, orientation, workspace, and interaction forces.

In an embodiment, the manipulator 106 is actuated by piezoelectric motors 412 and joint positions are sensed by optical encoders 414. The piezoelectric motors 412 are controlled by piezoelectric motor drivers 410. In a further embodiment, the piezoelectric motor drivers 410 are configured to minimize interference with the MRI scanner 408 and may include filtering. The motors 412 may be controlled to provide position control, speed control, or force control. Force control of the piezoelectric actuators may be accomplished by varying the drive waveform's amplitude, frequency, phase or other parameters to modify the friction between the driven element and the motion generating elements of motors 412. In an additional embodiment of the present invention the robotic manipulator 106 is teleoperated. In a further embodiment, haptic feedback may be available. The robot controller 106 may communicate directly with the motor drivers 410, or there may be an intermediate interface such as backplane with signal aggregator. In an embodiment, the piezoelectric motor drivers 410 and robot controller 406 are contained in controller 104 which is enclosed in an EMI shielded enclosure located in the MRI scanner room. In an alternate embodiment, the functionality of the robot controller 406 is integrated with the navigation software 402, and the workstation 102 (see FIG. 1) communicates directly with the motor divers 410 or corresponding interface. A modular system architecture allows the location of the breaks between software and hardware components to be adapted to a specific application.

Figure 5:
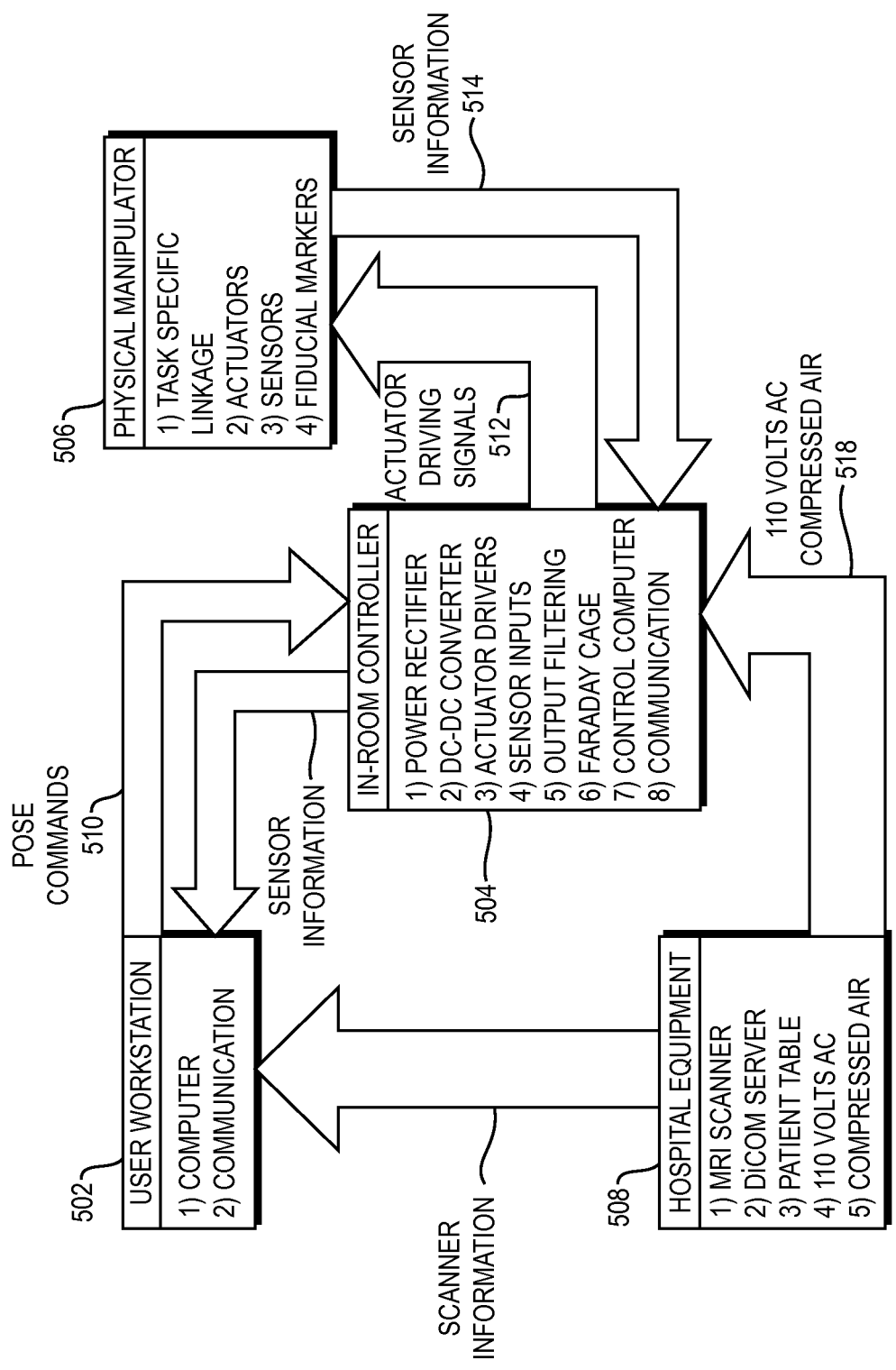
FIG. 5 is a schematic diagram of an embodiment of the system of this invention.

A specific embodiment of system 100 of the present invention is shown in FIG. 5. In FIG. 5, the user workstation 502 represents workstation 102 and includes a computer and a communication interface. In one embodiment, the communication interface is, but not limited to, a fiber optic Ethernet media converter. A set of coordinates for the end effector of the manipulator 506 (also 106) are selected, and sent to the controller 504 (also 104). In one embodiment, the controller 504 is enclosed in a Faraday cage forming an electro-magnetic interference (EMI) shielded enclosure and contains an AC-DC power rectifier, one or more low-noise, linear or low frequency switching DC-DC power converters, a control computer, actuator drivers with output filtering, sensor interfaces and a communication interface. The in-room controller 504 represents controller 104 and uses the kinematic information about the manipulator 506 (also 106) and the coordinate information to generate a planned pose for the manipulator 506. The physical manipulator 506 represents the manipulator 106, wherein it incorporates a task-specific end effector. The end effector may be in the form of a linkage mechanism. Further, the linkage mechanism itself may be unactuated and coupled to an actuator module to complete the manipulator 506 or 106. The manipulator 506 or 106 may also include sensors and fiducial markers. The pose is then achieved through manipulation of the individual actuators through drive signals 512 in a closed loop fashion utilizing sensor information 514 from the manipulator 506 itself. Once the controller 504 interprets that the manipulator 506 has reached the intended planned position, the workstation 502 utilizes a medical imaging system to verify the position of the manipulator's end effector. The medical imaging system may incorporate one or more of an MRI scanner, patient table, imaging coils, DICOM or other imaging server, power source and air supply as described in 508, which represent the hospital equipment 108. The power source and air supply 518 may be connected to the in-room robot controller 504. In one embodiment, the power source is, but may not limited to, approximately 110 volt AC power and a ground cable that is connected to the rectifier and DC-DC converted within controller 504.

Figure 6:
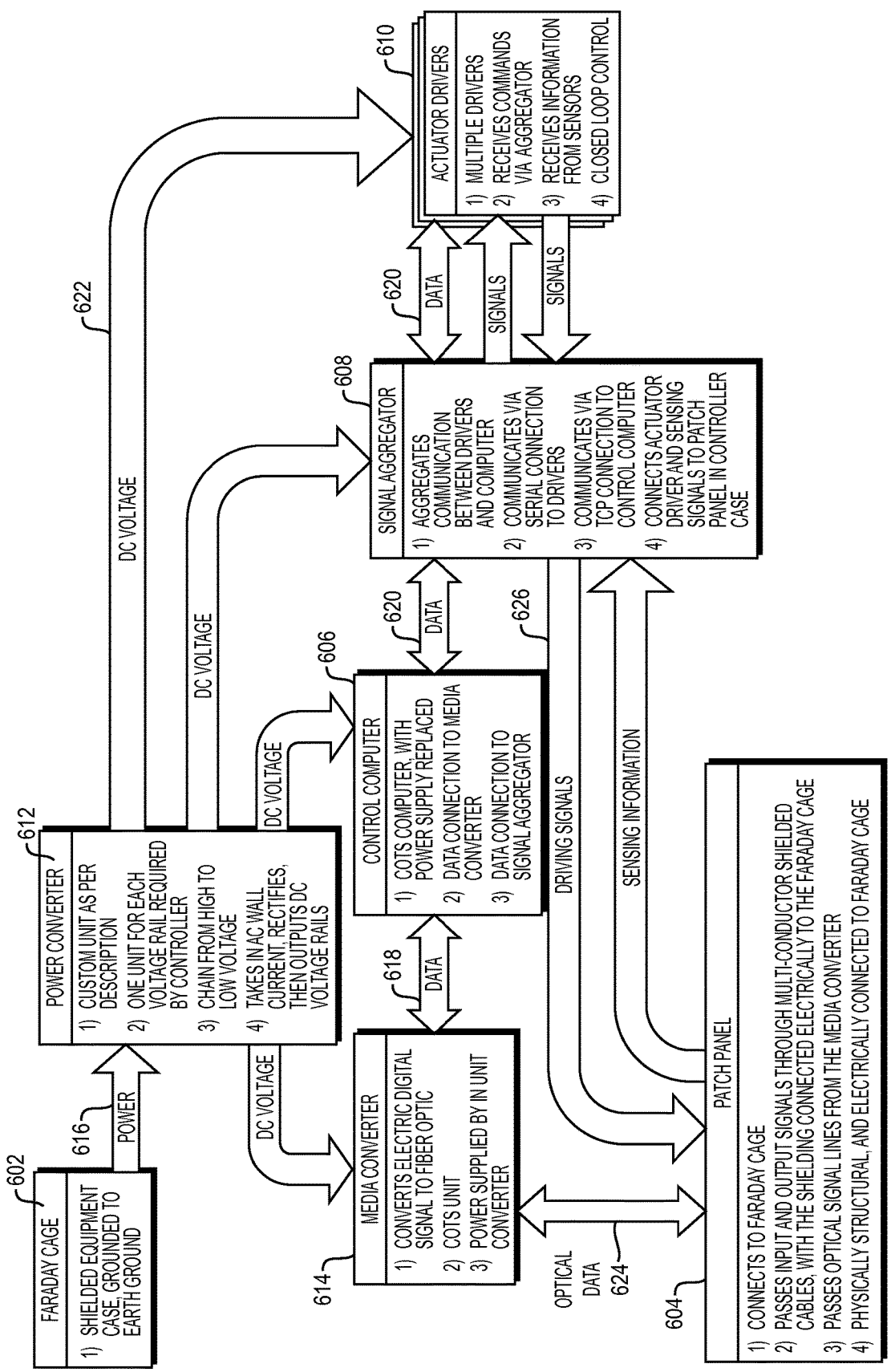
FIG. 6 is a schematic diagram of the components and connections of the controller.

Now referring to FIG. 6, the inner workings of one embodiment of the robot controller 504/104 is described. The continuous Faraday cage enclosure 602 houses the entirety of the controller equipment. The patch panel 604 acts to allow the passage of electrical and other forms of information and energy to be passed in and out of the enclosure 602 without allowing the escape of EMI. These connections include the optical data transfer connection 624 which the control computer uses to communicate with the workstation 502 (or 102), as well as the controller supply lines 616 and the actuator and sensor signals 626. The next piece of equipment is the controller computer 606 which is generally a common, off the shelf computer capable of running the software required to perform the operation described in FIG. 3. This is generally implemented as a common, off the shelf computer with the power supply removed so its electrical power can be supplied by the custom power converter 612. This device is connected via digital data connection to the signal aggregator 608, which can include, but is not limited to Transmission Control Protocol/Internet Protocol (TCP/IP), Universal Serial Bus (USB), Open Image Guided Therapy Link (OpenIGTLink), or others. The signal aggregator 608 is a device that manages the passage of information from the control computer 606 to the actuator drivers 610, and back through physical or data connections 620 and 628. Additionally, the signal aggregator 608 combines the driving signal and sensor information lines from the actuator drivers 610 to the multiconductor connector in the patch panel 604 via the multiconductor electrical data connection 626. Additionally, the media converter 614 communicates with the control computer via electrical data connection 618, and converts the media to an optical data stream that is passed out of the patch panel 604 through optical connection 624. Finally, all electrical devices within the enclosure get their power from the power converter 612, which is built later to supply all the required DC voltages, and connected to all supported equipment via the DC voltage rail connections 622.

Figure 7B:
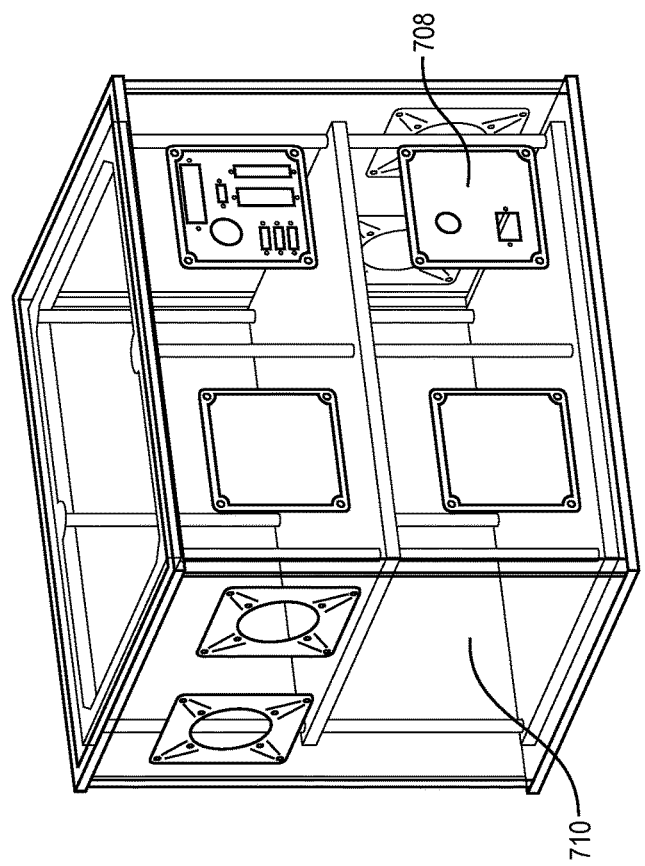
FIGS. 7A and 7B illustrate the modular equipment rack design of the Gausian cage for the controller without the feet shown.
Figure 7A:
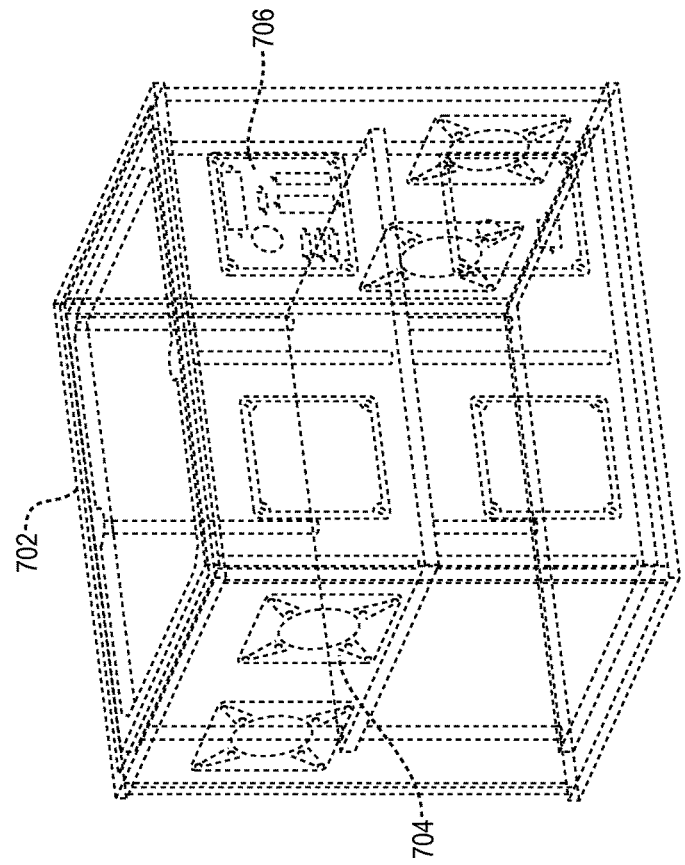

Continuing to FIGS. 7A and 7B, which is a diagram of the continuous Faraday cage enclosure, surrounding the controller equipment, the basic structure of this device is provided by the conductive paneling 710 which can be made of many materials such as, for example, but is not limited to, sheet aluminum, steel, or a non conductive material with a conductive coating. Cut into this sheeting is vent ports 704 which allow the exchange of air for the purposes of cooling, which have EMI shielding vents mounted to them. Additionally cut into the structural sheeting 710 is the port for the supply connection patch panel 708 (also 604) where the different electrical and non-electrical supplies are passed into the controller in a manner that shields EMI from escaping. These supplies can include, but are not limited to, AC wall current, compressed air, and DC voltage supplies. Additionally, cut into the structural sheeting 710 is the port for the manipulator connector patch panel 706 where the multi-element cables used to transfer driving signals and sensor information back and forth between the manipulator and the controller box. These elements can include, but are not limited to hydraulic, pneumatic, and electrical transfer lines. Finally, the cage FIG. 7A is completed with a lid 702 designed to be opened and closed more frequently than the patch panels and thus contains an EMI shielding gasket.

Figure 8:
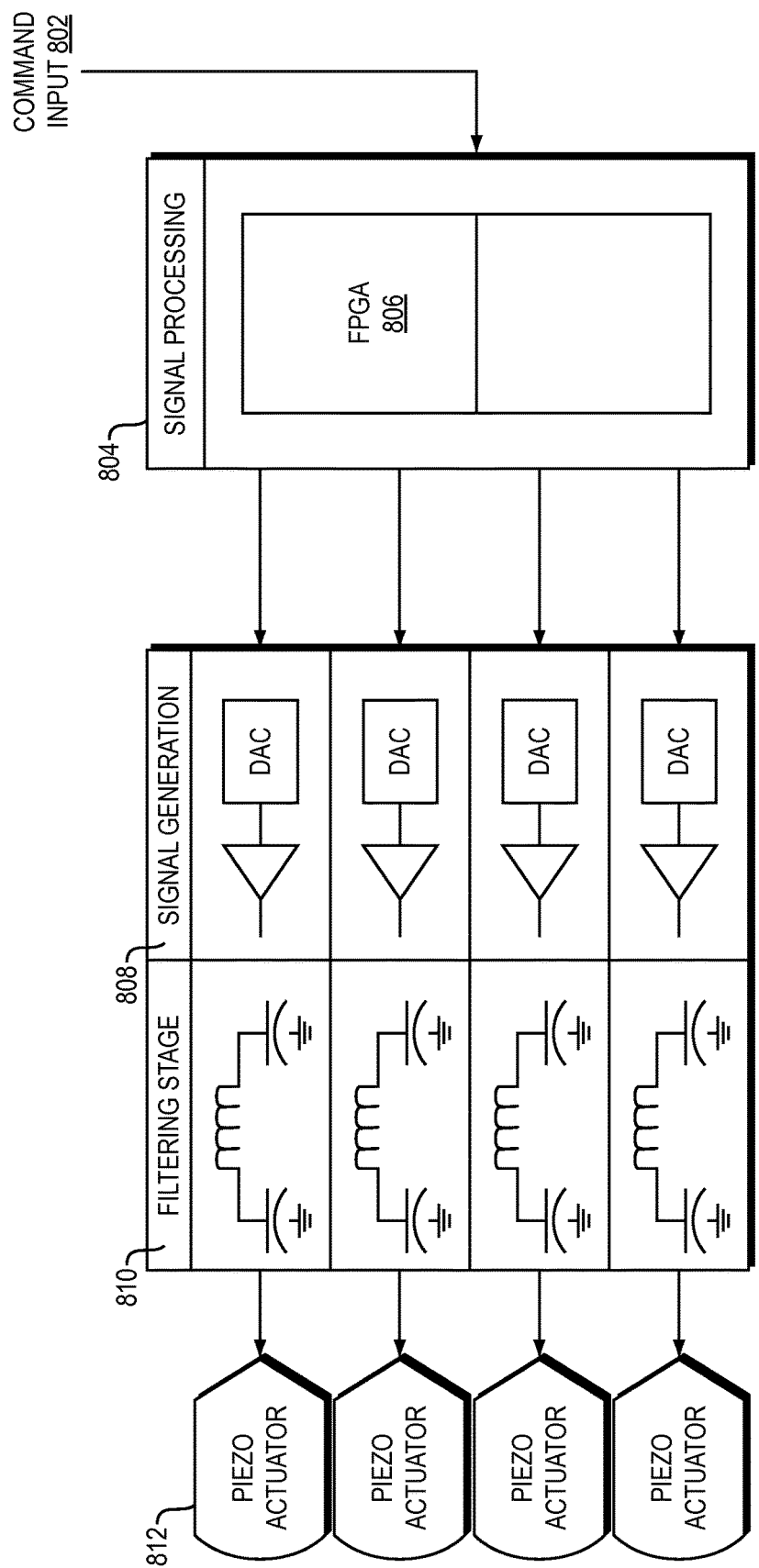
FIG. 8 illustrates schematically the power converter of the controller.

Referring now to FIG. 8, a general view of the internal operation of an actuator driver is shown, beginning with the command input 802 from the piezoelectric actuators which is fed into the signal processor 804. The command input can be comprised of a variety of forms of analog and digital data which may include, but is not limited to velocity, position, and force commands. The input 802 may be passed to the signal processor 804 via synchronous or asynchronous serial communication, Ethernet, USB, fiber optics, or other means. Driving signals are then produced and amplified in the signal generation segment 808, which can be comprised of but is not limited to, a series of operational amplifiers connected to the output of a digital to analog converter that receives the digital information from the signal processing unit or signal processor 804. The output of the signal generation segment 808 is then passed into the filtering stage 810 which is used to block bandwidths of electrical signals which may be in frequency ranges that cause unfavorable image distortion. The output of the filtering stage 810 is then sent to the piezoelectric actuators 802 via the multi-element shielded cable coming from the faraday cage 602 patch panel 604. The cables may terminate in a shielded breakout board on or near the manipulator 106 or connect directly to the actuators.

Figure 9:
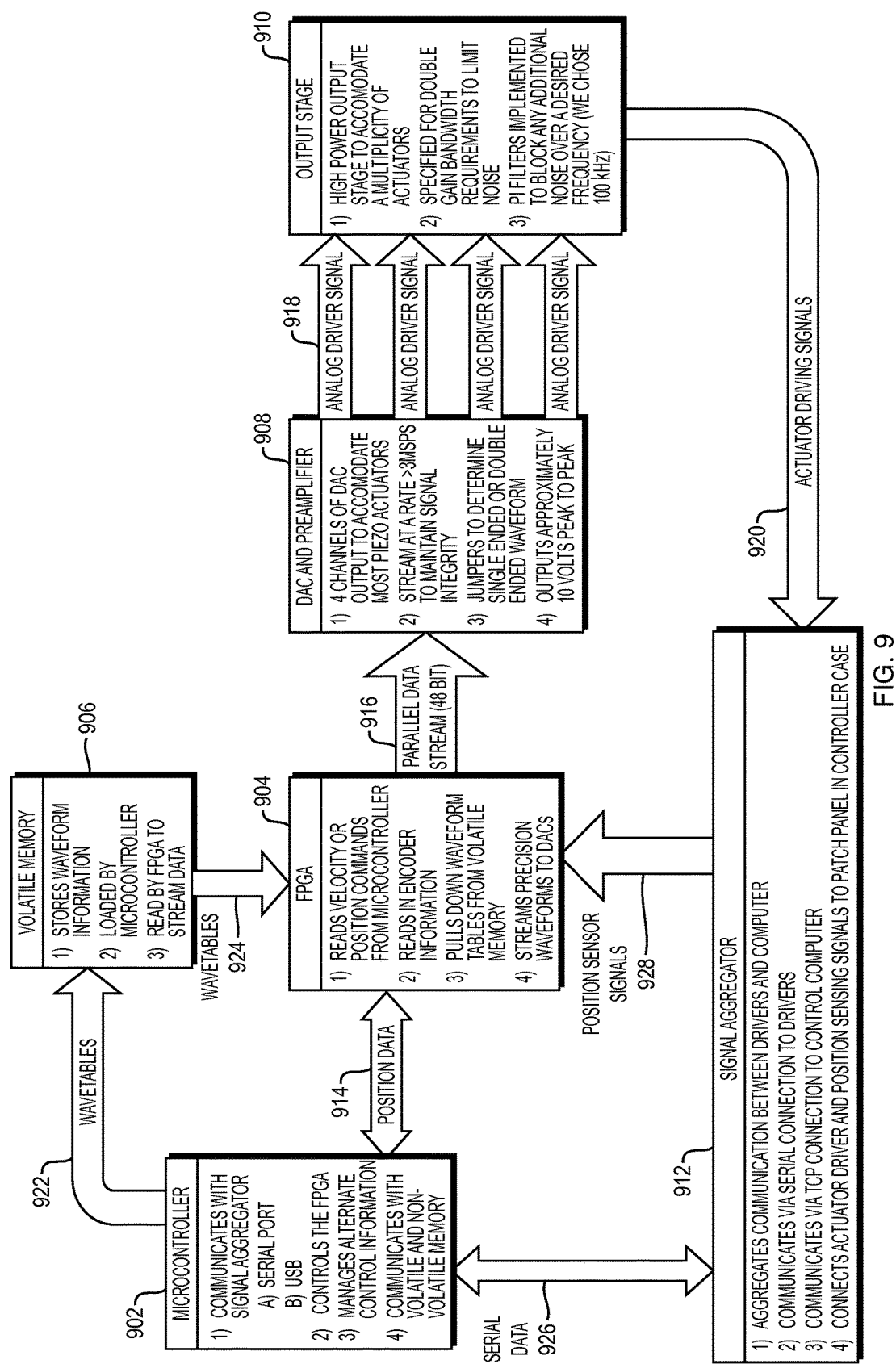
FIG. 9 is a schematic diagram of the actuator drivers of the controller.

Now referring to FIG. 9, the detailed internal function of one embodiment of the piezoelectric actuator driver 610. Initially command information 802 is passed from the signal aggregator 912 via the serial data connection 926 to the microcontroller 902. The microcontroller 902 in this embodiment has the function of handling communications with the aggregator 912, and control of the signal generator and sensing information. The microcontroller 902 communicates with the FPGA 904 via position data connection 914, as well as the volatile memory 906 via data connection (wavetables) 922. Data connection 922 where the data is in the form of waveform tables that are produced in analog form to drive piezoelectric actuators 804. The field programmable gate array (FPGA) 904, where the FPGA 904 is used to pull waveform information from the volatile memory 906 and use it to execute commands received over position data connection 914. Where FPGA 904 is also used to receive sensor information over position sensor signals 928 to be used for purposes including, but not limited to, execution of said commands received from microcontroller 902. Where the parallel data stream 916 produced by the FPGA 904 is then interpreted into analog actuator drawing signals 920, by first converting them into a low voltage analog waveform Connector 918 by the digital to analog converter (DAC) and preamplifier 908. The preamplifier 908, which can be comprised of, but is not limited to, high speed parallel digital to analog converters which can convert the digital waveform information stored in volatile memory 906. Once the low voltage analog driver signal 918 is produced, it is then amplified and filtered by the output stage 910 which is capable of multiplying the voltage and supplying a high amount of current. Components in this stage are overspecced in order to prevent noise.

Figure 10:
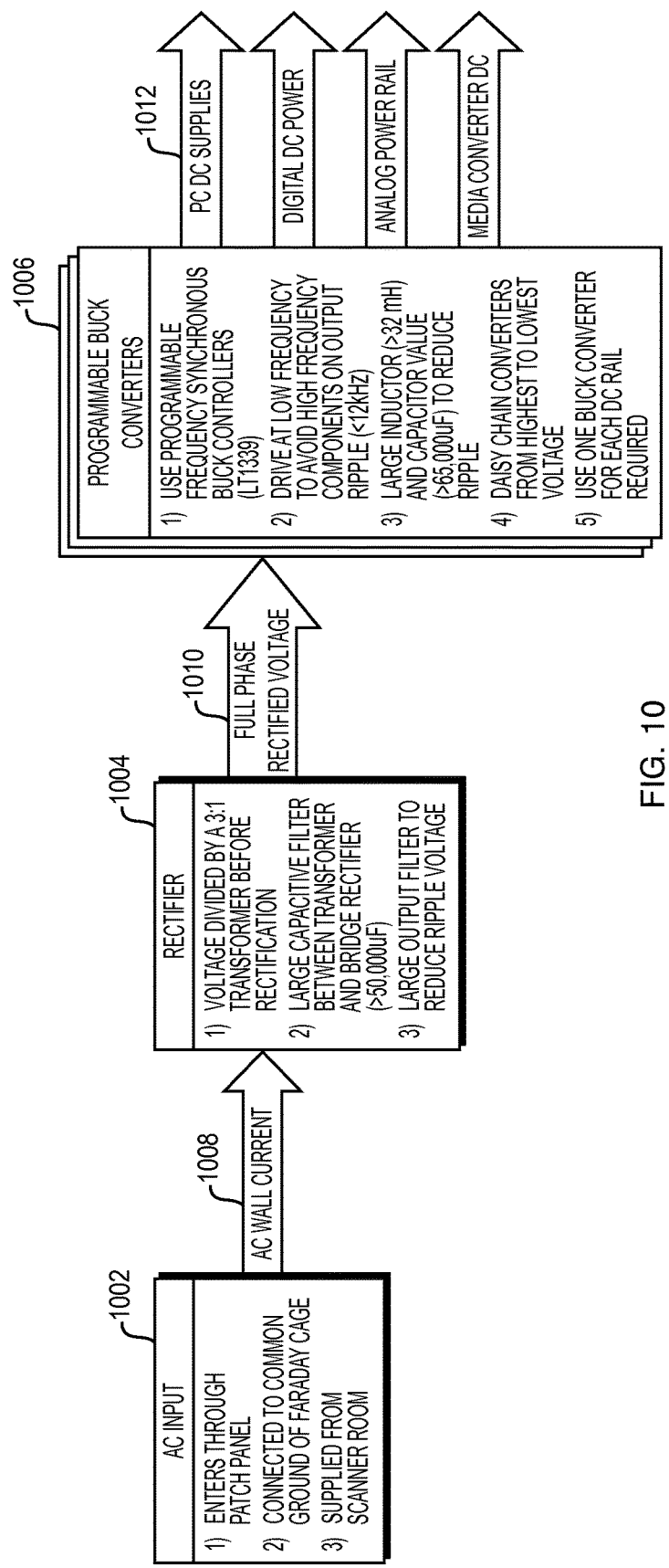
FIG. 10 is a schematic diagram of the power converter.

Referring now to FIG. 10, the power converter 612 as shown in FIG. 6 is supplied by the patch panel 604 via the AC input 1002. The AC input 1002 is carried by the wall current connector 1008 which is of the form of a cable rated to handle the electrical load required to operate the rest of the electrical equipment. This AC current is passed into the bridge rectifier 1004 where the voltage is divided before rectification to approximate the highest DC voltage required by the system. There is then a large capacitive filter pre and post rectification or full phase recited voltage 1010 in the rectifier 1004 to prevent rejection of noise back through the supply line and passing of noise to the converters. Once the input line is fully rectified and filtered 1006, it is then passed through the programmable buck converters 1006. Programmable converters are utilized so that the switching frequency can be controlled to prevent image degradation. Finally the DC voltage rails or supplies 1012 are passed out of the custom power converter 612 of signals via connection Referring now to FIG. 11 and FIGS. 12A and 12B, the kinematics of one embodiment of the manipulator 106 as per its design for use assisting with DBS electrode implantation. The first, second and third degree of freedom (DOF) are all contained within what is commonly called a prismatic XYZ stage labeled as the three DOF Translation Base 1102. The next two degrees of freedom are expressed as a two DOF remote center of motion style linkage 1104, where the RCM linkage can be described as, but is not limited to, mimicking the motion of a stereotactic neural insertion frame. The next two degrees of freedom are expressed as an optional yoke 1106 and increases 6 degrees of freedom to 8 degrees of freedom that can be used to achieve insertion angles other than those along the RCM axis. This allows the manipulator 106 to achieve greater degrees of dexterity. The final axis which is, but is not limited to, a passive insertion axis 1108, where the surgeon may manually insert an electrode. FIGS. 11B and 11C show pictorially how the manipulator allows for 8 degrees of freedom and can be used with a skull in a DBS electrode implementation. The design is not restricted to six or eight DOF, alternate embodiments may encompass other numbers of degrees of freedom. Alternate specific applications will result in alternate mechanism designs.

Figure 12A:
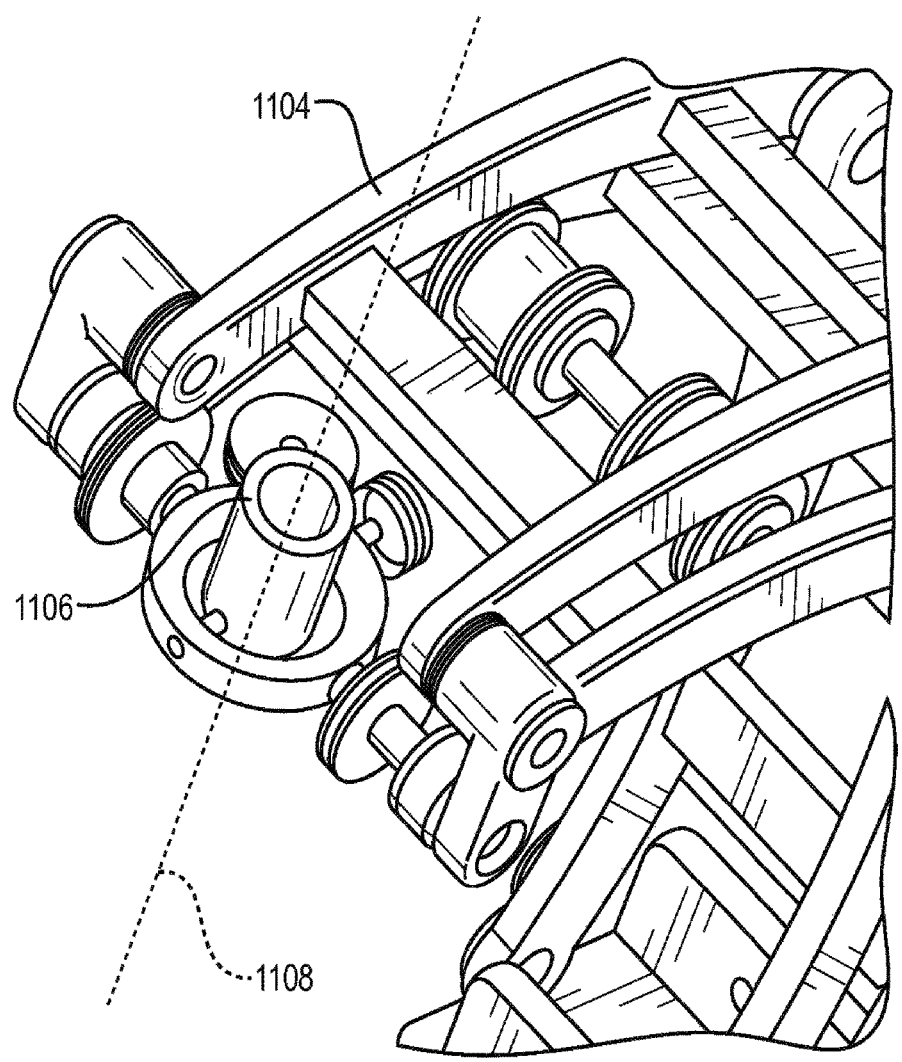
FIG. 12A illustrates the three degrees of freedom 6, 7 and 8 of FIG. 11 provided by the yolk of the manipulator.
Figure 12B:
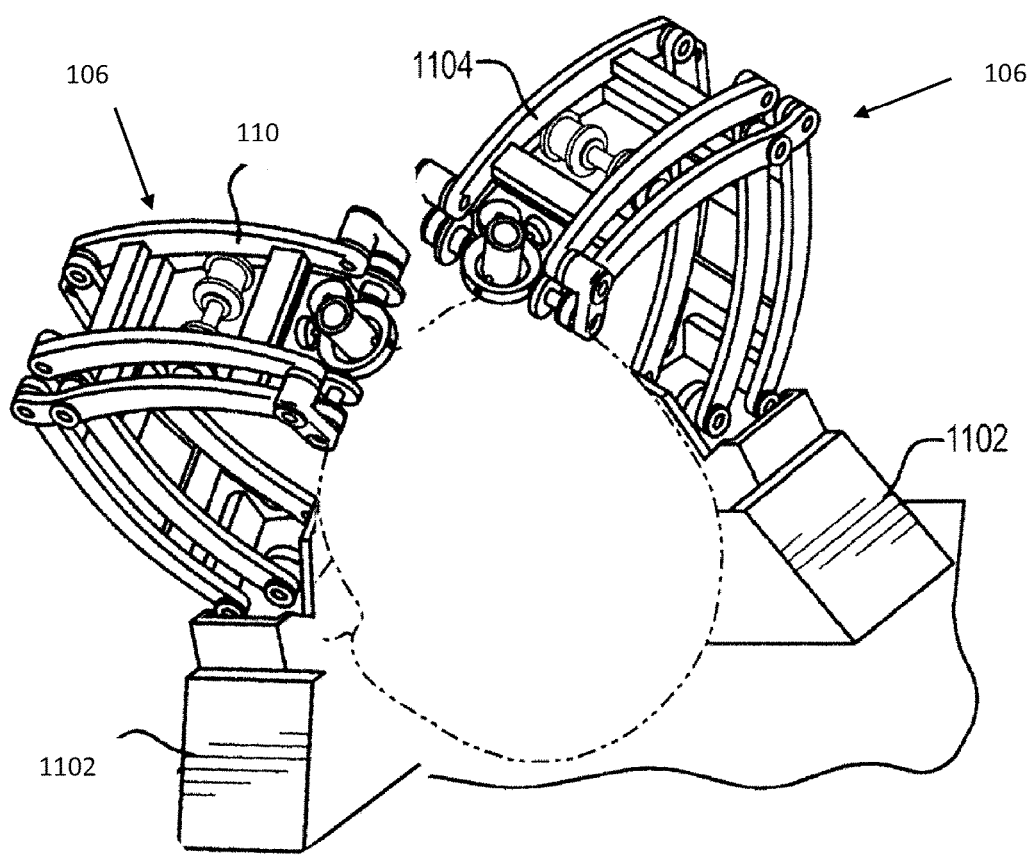
FIG. 12B illustrates the three degrees of freedom provided by a prismatic X-Y-Z-stage as the manipulator is used with a skull.
Figure 13:
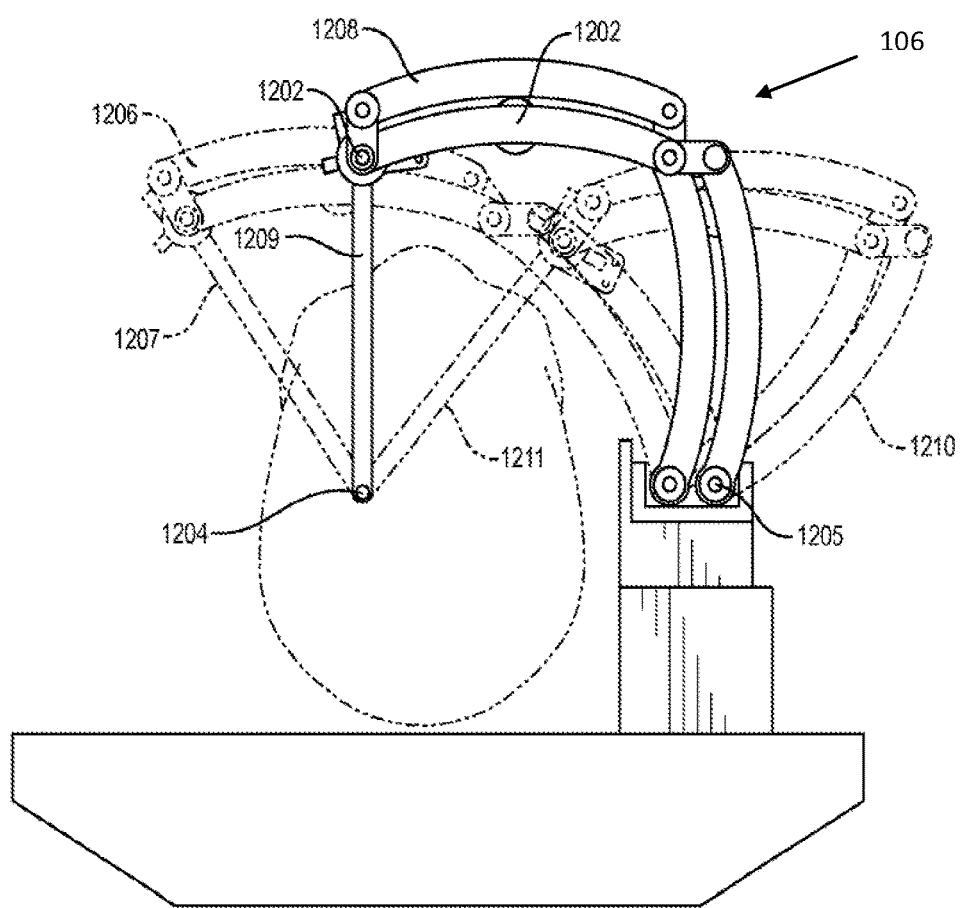
FIG. 13 is a schematic depiction of an embodiment of the manipulator with six degrees of freedom.

Referring now to FIGS. 12A and 12 B, the manipulator 106 described earlier in a specific embodiment of said manipulator 106 adapted for DBS electrode insertion. The manipulator 106 can be constructed of rigid plastic links 1208 pin jointed 1202 via non conductive rods with plastic sleeve bearings 1205 as shown in FIG. 13 and may be used at all pin joint locations. The RCM point 1204 is clearly shown, and is targeted through all positions of the manipulator sweep 1207-1211 allowing a single target point 1204 to be reached from multiple insertion angles 1207, 1209, 1211 shown in FIG. 13 represents three manipulator configurations overlaid to demonstrate the mechanically constrained rotation center concept generated by motions 1104. This mimics the motion of a standard stereotactic insertion frame. The rotation center may be placed at or near the target or it may be placed at or near the skull entry point. Additional dexterity afforded by the extra degrees of freedom of yolk 1106 enables repositioning of the rotation center though software control. The 3 DOF translation base can be used to change the position of the remote center of motion point. An enlarged view of FIG. 11B is shown and FIG. 13 to show the extra DOF 6 and 7.

The configuration of a specific embodiment of system 100 of the present invention is shown in FIG. 14. Patient 1402 is placed inside MRI scanner 1404 located in MRI scanner room 1400 and rests upon scanner bed 1406. Patient's head 1408 rests upon an integrated head rest platform 1412. Head fixation 1414 maintains head position relative to the platform 1412. MRI imaging coil 1418 is coupled to platform 1412. In one embodiment imaging coil 1418 is a standard head coil, surface coils, or other readily available imaging coil. Alternatively, imaging coil 1418 may be specific for this system. In one embodiment, the imaging coil 1418 is actuated and reconfigurable. Robot base 1420 is fixed to platform 1412. Manipulator 1422 (also 106) sits upon platform 1412. In one embodiment, robot base 1420 is a prismatic motion stage for positioning and the manipulator 106 and provides 3 degrees of freedom for manipulator 106. The manipulator 106 may be application-specific or patient-specific. In one embodiment, the manipulator 1422 may be in itself unactuated base and coupled to an actuation module 1420 as described earlier. The robotic device comprising base 1420 and line manipulator 1422, and also representing 106, is coupled to the controller 1430 via line 1432. In one embodiment, line 1432 is a shielded multiconductor cable transmitting motor power from the controller to piezoelectric motors in the robotic device or manipulator 1422 or 106 (not shown) and receiving encoder signals from the robotic device to the controller. In one embodiment, one or more breakout boards are coupled to platform 1412 or robot base 1420 to distribute control and sensor signals. In an alternate embodiment, pneumatic or hydraulic power may be transmitted via line 1432. Alternatively, line 1432 may include fiber optic communications. In one embodiment, controller 1430, which also represents 104, is also coupled to imaging coil 1418 via cable 1434 for control of the imaging coil configuration. Controller 1430 receives power via cable 1438 from the MRI scanner room. Power may include AC electricity and a ground connection. Connection 1438 may also include pressurized fluid such as air or nitrogen. Controller 1430 is communicatively couple to workstation 1450 or 102 via cable or other coupling 1440. Cable 1440 may be a fiber optic communication cable that passes through waveguide 1444 in the wall 1446 of the MRI scanner room 1400. Workstation 1450 represents user workstation 102 and may be located in the MRI console or control room 1452 as described earlier.

Although the invention has been decided with various embodiments, it should be realized that this invention is also capable of further and other embodiments within the spirit and scope of the appended claims.

What is claimed is:

1. A modular system for use with a manipulator selected from a plurality of manipulators for a medical procedure, the modular system configured for providing an image guided assisted medical procedure, the modular system comprising:
    a plurality of computer controlled actuators coupled to the manipulator;
    a controller configured for defining from one to eight degrees of freedom of movement of an instrument and identifying linkages that are configured for performing movements of at least one degree of freedom of movement of said one to eight degrees of freedom,
    wherein the controller is connected to said actuators and configured for providing signals to the actuators in order to move the manipulator from one to eight degrees of freedom for creating computer controlled motion of the manipulator, at least one degree of freedom of movement of said one to eight degrees of freedom is along a passively guided unactuated insertion axis including at least one of a sensor or a tracking fiducial marker, said controller and said actuators also configured to operate with alternate manipulators selected from the plurality of manipulators by identifying linkages of the at least one alternate manipulators for performing at least one motion, and selecting actuators and sensors for connecting to said linkages of the at least one alternate manipulator for controlling movements thereof;
    an imaging device, comprising a magnetic resonance imaging (MRI) system including a bore, the MRI system enabling visualization of a tissue at said medical procedure; and
    a computer communicatively coupled to said MRI system and said controller,
    wherein the manipulators are provided and configured to operate within the bore of the MRI system during said medical procedure, and
    wherein the computer is configured to collect and process images from said MRI system, and further configured to instruct said controller to direct under computer control the plurality of manipulators via said signals to the actuators to move the plurality of manipulators based upon said images collected by said computer from said MRI system.

2. The system of claim 1, wherein said medical procedure is a surgical procedure.

3. The system of claim 2, wherein said surgical procedure is a thermal ablation procedure.

4. The system of claim 2, wherein said surgical procedure is a deep brain stimulation procedure.

5. The system of claim 2, wherein said MRI system further comprises an MRI scanner, and wherein the surgical procedure is performed in the presence of said MRI scanner.

6. The system of claim 5, wherein said MRI system further comprises an imaging coil defining an opening, and wherein said controller is connected to said MRI imaging coil and configured to direct the orientation of said coil so as and further configured to align the opening of the coil with a planned trajectory.

7. The system of claim 5, wherein at least part of the surgical procedure is performed within the MRI scanner.

8. The system of claim 7, wherein interactively updated MRI images are used to guide the image guided assisted medical procedure.

9. The system of claim 1, wherein said manipulator comprises two separable components in the form of said actuator and an application specific or patient specific mechanism.

10. A modular system for an image guided robotic assisted medical procedure, the modular system comprising:
a manipulator for performing a stereotactic neurosurgical procedure within a bore of a magnetic resonance imaging (MRI) system;
a plurality of computer controlled actuators coupled to said manipulator;
a controller configured for defining from one to eight degrees of freedom of movement of an instrument and identifying linkages that are configured for performing movements of at least one degree of freedom of movement of said one to eight degrees of freedom,
wherein the controller is connected to said actuators and configured for providing signals to said actuators in order to move said manipulator in at least one degree of freedom for creating computer controlled motion thereof,
said at least one degree of freedom being one of said one to eight degrees of freedom being required for performing the stereotactic neurosurgical procedure,
wherein at least one degree of freedom of movement of said one to eight degrees of freedom is along a passively guided unactuated insertion axis including at least one of a sensor or a tracking fiducial marker, said controller and said actuators further configured for coupling to and directing at least one alternative manipulator by identifying linkages of the at least one alternate manipulator for performing at least one motion, and selecting actuators and sensors for connecting to said linkages of the at least one alternate manipulator for controlling movements thereof;
wherein the MRI system is configured for enabling visualization of a tissue at said stereotactic neurosurgical procedure; and
a computer communicatively coupled to the MRI system and said controller,
wherein said computer collects and processes images from said MRI system and instructs said controller to direct said manipulators under computer control via said signals to the actuators to move said manipulators based upon said images collected by said computer from said MRI system in order to perform the stereotactic neurosurgical procedure.

11. The system of claim 10, wherein said manipulator is designed to operate without degradation of MRI image quality.

12. The method of claim 10, wherein said manipulator comprises two separable components in the form of said actuators and an application specific or patient specific mechanism.

13. The system of claim 10, wherein said surgical procedure is a deep brain stimulation procedure.

14. The system of claim 5, wherein the manipulator is further configured to operate under computer control inside the MRI scanner.

15. The system of claim 14, further configured to utilize in situ live MRI guidance to direct said manipulator under computer control inside the MRI scanner while said MRI scanner is imaging.

16. A method for image guided robotic assisted medical procedure, the method comprising:
identifying an area of a body for a medical procedure;
defining from one to eight degrees of freedom of movement of an instrument, at least one degree of freedom of movement of said one to eight degrees of freedom being required for performing the medical procedure, wherein at least one degree of freedom of movement of said one to eight degrees of freedom is along a passively guided unactuated insertion axis including at least one of a sensor or a tracking fiducial marker;
coupling a manipulator to a plurality of computer controlled actuators, the manipulator configured for performing the medical procedure within a bore of an MRI device, the coupling further comprising
identifying linkages for performing said movement along said at least one degree of freedom of movement, and
selecting at least one of said actuators and said at least one of a sensor or a tracking fiducial marker for connecting to said linkages for controlling movements thereof;
communicatively coupling a computer to said MRI device and a controller for providing signals; and
connecting said manipulator to the controller for moving said manipulator under computer control via the signals to the actuators based upon images collected by the controller from the MRI device,
wherein the controller is further configured for coupling to and directing at least one alternate manipulator adapted for said medical procedure by identifying linkages of the at least one alternate manipulator for performing at least one motion, and selecting actuators and sensors for connecting to said linkages of the at least one alternate manipulator for controlling movements thereof based upon images collected by the controller from the MRI device.

17. The method of claim 16, wherein the medical procedure is deep brain stimulation lead placement.

18. The method of claim 16, wherein the manipulator encompasses at least one actuator for actuating said one to eight degrees of freedom of movement of the instrument, wherein said actuator is coupled to linkages for performing at least one movement.

19. The method of claim 18, wherein at least one degree of freedom of movement of said one to eight degrees of freedom of movement is an insertion movement.

20. The method of claim 16, wherein at least part of the manipulator is application specific.

* * * * *